(12) United States Patent
Feng et al.

(10) Patent No.: US 12,709,728 B2
(45) Date of Patent: Aug. 18, 2026

(54) DEVICE FOR ENRICHMENT CULTURE AND GRAVITY-TYPE ISOLATION OF MARINE MICROORGANISMS IN HIGH-PRESSURE ENVIRONMENT

(71) Applicants: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

(72) Inventors: Jingchun Feng, Guangdong (CN); Si Zhang, Guangdong (CN); Zhifeng Yang, Guangdong (CN); Yi Wang, Guangdong (CN); Yanpeng Cai, Guangdong (CN); Song Zhong, Guangdong (CN)

(73) Assignees: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

( * ) Notice: Subject to any disclaimer, the term of this patent is extended or adjusted under 35 U.S.C. 154(b) by 637 days.

(21) Appl. No.: 18/020,266

(22) PCT Filed: Mar. 30, 2022

(86) PCT No.: PCT/CN2022/084121
§ 371 (c)(1),
(2) Date: Feb. 8, 2023

(87) PCT Pub. No.: WO2023/173495
PCT Pub. Date: Sep. 21, 2023

(65) Prior Publication Data

US 2024/0124827 A1 Apr. 18, 2024

(30) Foreign Application Priority Data

Mar. 17, 2022 (CN) ......................... 202210264680.2

(51) Int. Cl.
*C12M 1/00* (2006.01)
*C12M 1/06* (2006.01)
*C12M 1/34* (2006.01)

(52) U.S. Cl.
CPC ............ *C12M 41/40* (2013.01); *C12M 23/38* (2013.01); *C12M 23/58* (2013.01); *C12M 27/02* (2013.01); *C12M 29/20* (2013.01); *C12M 41/12* (2013.01)

(58) Field of Classification Search
CPC ...... C12M 41/40; C12M 23/38; C12M 23/58; C12M 27/02; C12M 29/20; C12M 41/12; C12M 41/48; C12M 47/12; C12M 33/22
See application file for complete search history.

(56) References Cited

U.S. PATENT DOCUMENTS

2010/0269761 A1 10/2010 Nien
2011/0068057 A1 3/2011 Haley, III et al.

FOREIGN PATENT DOCUMENTS

CN 101845406 9/2010
CN 103484355 1/2014
(Continued)

OTHER PUBLICATIONS

Edited by Zhanjiang Fishery College, "Marine Fish Food Organism Culture", Agriculture Press, with English translation thereof, Jun. 30, 1980, pp. 1-6.
(Continued)

*Primary Examiner* — Liban M Hassan
(74) *Attorney, Agent, or Firm* — JCIPRNET

(57) ABSTRACT

The present invention provides a device for enrichment culture and gravity-type isolation of marine microorganisms
(Continued)

in a high-pressure environment. The device includes an enrichment and multistage purification unit and a gravity-type isolation and culture unit. Under a high-pressure and low-temperature environment constructed to be consistent with a marine environment, the enrichment and multistage purification unit is used for realizing a process of enrichment and multistage purification of the marine microorganisms, obtaining a marine microorganism enrichment bacteria liquid and injecting the marine microorganism enrichment bacteria liquid into the gravity-type isolation and culture unit. The gravity-type isolation and culture unit is used for carrying out automatic streaking by means of gravity in the high-pressure environment to achieve solid isolation and culture of the marine microorganisms, such that culturability of the marine microorganisms is effectively improved.

14 Claims, 5 Drawing Sheets

(56) References Cited

FOREIGN PATENT DOCUMENTS

| | | |
|---|---|---|
| CN | 103540522 | 1/2014 |
| CN | 104498349 | 4/2015 |
| CN | 105754852 | 7/2016 |
| CN | 106336004 | 1/2017 |
| CN | 108179100 | 6/2018 |
| CN | 208098019 | 11/2018 |
| CN | 208234905 | 12/2018 |
| CN | 209024535 | 6/2019 |
| CN | 110591893 | 12/2019 |
| CN | 111477084 | 7/2020 |
| CN | 111551390 | 8/2020 |
| CN | 111551671 | 8/2020 |
| CN | 111894529 | 11/2020 |
| CN | 112964833 | 6/2021 |
| CN | 113051710 | 6/2021 |
| CN | 215517424 | 1/2022 |
| CN | 114127248 | 3/2022 |
| EP | 3091068 | 11/2016 |
| GB | 1324229 | 7/1973 |
| JP | 863267262 | 11/1988 |
| JP | H0440884 | 2/1992 |
| KR | 100809836 | 3/2008 |
| WO | 9600794 | 1/1996 |
| WO | 02059351 | 8/2002 |

OTHER PUBLICATIONS

Wendong Xian et al., “Research status and prospect on bacterial phylum Chloroflexi”, Acta Microbiologica Sinica, with English abstract, Aug. 17, 2020, pp. 1801-1820.

Jianzhen Liang et al., “Role of deep-sea equipment in promoting the forefront of studies on life in extreme environments”, iScience, Nov. 19, 2021, pp. 1-21.

Feng Jingchun et al., “Environmental and Ecological Protection Equipment in Deep Sea”, Strategic Stude of CAE, with English abstract, Nov. 9, 2020, pp. 56-66.

Dai; Jinping et al., “The application of molecular biology technology in the diversity study of methane—producing archaea”, Heilongjiang Animal Science and Veterinary Medicine, Feb. 2016, with English abstract, pp. 43-46, No. 2.

Shimshon Belkin et al., “Ocean and Health: Pathogens in the Marine Environment”, Jul. 2015, with partial English translation thereof, pp. 1-8.

Fengping Wang et al., “Biodiversity of deep-sea microorganisms”, Biodiversity Science, Jul. 2013, with English abstract, pp. 445-455, vol. 21, No. 4.

Li; Jiang et al., “Advances in Research on Anaerobic Methanotrophs”, Chin J Appl Environ Biol, Oct. 25, 2011, with English abstract, pp. 763-766, vol. 17, No. 5.

“International Search Report (Form PCT/ISA/210) of PCT/CN2022/084121,” mailed on Dec. 15, 2022, pp. 1-5.

Li Shi-Lun et al., “Control system of simulating platform for deep-sea extreme environment,” Journal of Zhejiang University(Engineering Science), vol. 39, Nov. 2005, pp. 1769-1772.

Jiang Kai et al., “Equipment simulating seefloor extreme environment with remote monitor function,” Chinese Journal of Scientific Instrument, vol. 27, Sep. 2006, pp. 1095-1099.

DEVICE FOR ENRICHMENT CULTURE AND GRAVITY-TYPE ISOLATION OF MARINE MICROORGANISMS IN HIGH-PRESSURE ENVIRONMENT

CROSS-REFERENCE TO RELATED APPLICATION

This application is a 371 of international application of PCT application serial no. PCT/CN2022/084121, filed on Mar. 30, 2022, which claims the priority benefit of China application no. 202210264680.2, filed on Mar. 17, 2022. The entirety of each of the above mentioned patent applications is hereby incorporated by reference herein and made a part of this specification.

TECHNICAL FIELD

The present invention relates to the technical field of marine microorganisms, in particular to a device for enrichment culture and gravity-type isolation of marine microorganisms in a high-pressure environment.

BACKGROUND

Marine microorganism resources are globally important strategic resources with the largest biodiversity. Technologies such as molecular ecology and macrogenomics have significantly increased our knowledge of marine microorganism diversity. However, currently 99% of marine microorganisms are not purely cultured, while many genes have unknown functions that are not annotated or may be misannotated in databases. As a result, modern histological techniques are insufficient to provide sufficient information for understanding all microorganisms, especially those that have not been classified yet. Improving the culturability of uncultured microorganisms and innovating pure culture methods are important ways to interpret phenotypes and genotypes of the microorganisms.

Although solutions disclosed in the prior art can achieve enrichment culture of the microorganisms in a deep-sea in-situ state, the solutions do not carry out isolation and culture of the marine microorganisms, and the successful rate of culture cannot be effectively increased.

SUMMARY

In order to overcome at least one of the above technical defects, the present invention provides a device for enrichment culture and gravity-type isolation of marine microorganisms in a high-pressure environment aiming at characteristics of an extreme environment in which the marine microorganisms live. By reconstructing an in-situ environment for enrichment culture and isolation of the marine microorganisms, the culturability of the marine microorganisms is effectively improved, and an important basic means is provided for development and utilization of deep-sea microorganism resources.

In order to solve the above-mentioned technical problems, the present invention adopts the following technical solutions.

This solution provides a device for enrichment culture and gravity-type isolation of marine microorganisms in a high-pressure environment. The device includes an enrichment and multistage purification unit, a gravity-type isolation and culture unit, a temperature controlling system, a pressure control system, and a central control system; control ends and signal detection ends of the enrichment and multistage purification unit and the gravity-type isolation and culture unit are electrically connected to the central control system; control ends of the temperature controlling system and the pressure control system are electrically connected to the central control system; the enrichment and multistage purification unit is used for realizing a process of enrichment and multistage purification of the marine microorganisms, obtaining a marine microorganism enrichment bacteria liquid, and injecting the marine microorganism enrichment bacteria liquid into the gravity-type isolation and culture unit; the gravity-type isolation and culture unit is used for carrying out automatic streaking by means of gravity in the high-pressure environment to achieve solid isolation and culture of the marine microorganisms, such that culturability of the marine microorganisms is effectively improved; and the temperature controlling system and the pressure control system are connected to the enrichment and multistage purification unit and the gravity-type isolation and culture unit for constructing a high-pressure and low-temperature environment consistent with a marine environment in the enrichment and multistage purification unit and the gravity-type isolation and culture unit, so as to ensure that enriched deep-sea microorganisms are enriched, purified, separated and cultured under in-situ environmental conditions.

In the above-mentioned solution, the enrichment and multistage purification unit may achieve enrichment culture of the microorganisms under marine in-situ temperature and pressure environmental conditions, and the gravity-type isolation and culture unit may achieve isolation and culture of the marine microorganisms. By reconstructing the in-situ environment for enrichment culture and isolation of the marine microorganisms, the problem about isolation and pure culture of the marine microorganisms in the high-pressure environment is solved, the culturability of the marine microorganisms is effectively improved, and an important basic means is provided for development and utilization of deep-sea microorganism resources.

In the above-mentioned solution, the central control system is used for realizing monitoring of changes of various environmental data information, as well as real-time acquisition, processing, storage, image output, and other functions during enrichment, isolation and purification of microbial enrichment bacteria in the high-pressure environment.

In the above-mentioned solution, a pressure environment at a water depth greater than 200 meters in the deep sea is theoretically considered as the high-pressure environment, and a water temperature environment below 4° C. in the deep sea is theoretically considered as the low-temperature environment. In this solution, a corresponding high-pressure and low-temperature environment is constructed according to a culture environment of marine microorganisms to be cultured.

The enrichment and multistage purification unit includes a plurality of microbial liquid enrichment culture chambers connected in series; the microbial liquid enrichment culture chambers are provided with removable sealing lids and connection and sampling valve sets, and sensor sets are disposed inside the microbial liquid enrichment culture chambers; each of the microbial liquid enrichment culture chambers is disposed in the temperature controlling system; the removable sealing lids are used for facilitating sterilization operations and placement of culture substrates inside the microbial liquid enrichment culture chambers; the connection and sampling valve sets are used for connection and sampling of the microbial liquid enrichment culture chambers, and are connected to the pressure control system for feeding liquid or gas into the microbial liquid enrichment culture chambers to increase pressure inside the microbial liquid enrichment culture chambers, such that pressure values in the microbial liquid enrichment culture chambers are consistent with actual conditions in a deep sea; the sensor sets are used for real-time monitoring of temperature and pressure changes in the microbial liquid enrichment culture chambers, and transmitting signals to the central control system; and a last microbial liquid enrichment culture chamber of the enrichment and multistage purification unit is connected to the gravity-type isolation and culture unit through a connection and sampling valve set.

The microbial liquid enrichment culture chambers are further provided with stirring rods, and the stirring rods are used for enhancing a reaction process of a substrate in a culture process of the microbial liquid enrichment culture chambers.

In the above-mentioned solution, the stirring rods are manual stirring rods, and may enhance mass transfer through intermittent manual stirring, or enhanced continuous or intermittent stirring rods may be placed as needed for enhancing the reaction process of the substrate in the culture process, thereby increasing energy and nutrient supply to the microorganisms and improving culture efficiency.

The sensor sets include temperature sensors and pressure sensors; the temperature sensors are used for real-time monitoring of temperature changes in the microbial liquid enrichment culture chambers; the pressure sensors are used for real-time monitoring of pressure changes in the microbial liquid enrichment culture chambers; and signal output ends of the temperature sensors and signal output ends of the pressure sensors are electrically connected to the central control system.

The connection and sampling valve sets include liquid inlet valves, gas inlet valves, sampling valves, and liquid outlet valves; the microbial liquid enrichment culture chambers are connected in series via the liquid outlet valves and the liquid inlet valves, and a liquid outlet valve of a former microbial liquid enrichment culture chamber is connected to a liquid inlet valve of a latter microbial liquid enrichment culture chamber; a liquid outlet valve of the last microbial liquid enrichment culture chamber is connected to the gravity-type isolation and culture unit; the gas inlet valves are connected to the pressure control system for feeding gas into the microbial liquid enrichment culture chambers to increase the pressure in the microbial liquid enrichment culture chambers, such that the pressure values in the microbial liquid enrichment culture chambers are consistent with the actual conditions in the deep sea; and the sampling valves are used for real-time sampling and analysis of the microorganisms in the microbial liquid enrichment culture chambers, so as to regulate corresponding environmental parameters and optimize the enrichment culture process.

In the above-mentioned solution, the plurality of microbial liquid enrichment culture chambers are connected in series to form the enrichment and multistage purification unit, a bacteria liquid in the former microbial liquid enrichment culture chamber enters the next microbial liquid enrichment culture chamber through pressure-holding transfer. On this basis, through concentration gradient dilution, a microbial bacteria liquid obtained in the last microbial liquid enrichment culture chamber may be functional microorganisms enriched and highly purified in a high-pressure environment and under supply stress of directed nutrient conditions. Pressure-holding transfer may be achieved by sampling the enrichment liquid from the former microbial liquid enrichment culture chamber by a microinjection pump through the sampling valves and then pumping the enrichment liquid into the latter microbial liquid enrichment culture chamber. Also, pressure of the latter microbial liquid enrichment culture chamber may be increased to be slightly smaller than pressure of the former microbial liquid enrichment culture chamber, then the liquid outlet valve of the former microbial liquid enrichment culture chamber and the liquid inlet valve of the latter microbial liquid enrichment culture chamber are opened, and the microbial enrichment liquid may automatically enter the latter microbial liquid enrichment culture chamber from the former microbial liquid enrichment culture chamber for dilution culture under the condition of a small pressure difference. In the whole enrichment culture process, the temperature and pressure environmental conditions in the microbial liquid enrichment culture chambers are consistent with the environmental conditions of the microorganisms in the deep sea to ensure validity of enrichment culture.

The gravity-type isolation and culture unit includes an isolation and culture chamber, a liquid injection unit, and an environmental parameter detection unit; the gravity-type isolation and culture unit is connected to the last microbial liquid enrichment culture chamber of the enrichment and multistage purification unit through the liquid injection unit; a microorganism isolation branch is disposed in the isolation and culture chamber for carrying out an isolation operation on microorganisms to provide a maximum area for microorganism culture; a central liquid injection pipe is disposed on a top of the isolation and culture chamber, and the isolation and culture chamber is connected to the liquid injection unit through the central liquid injection pipe; a marine microorganism enrichment bacteria liquid is injected by the liquid injection unit into the microorganism isolation branch of the isolation and culture chamber; the isolation and culture chamber is disposed in the temperature controlling system and connected to the pressure control system for constructing the high-pressure and low-temperature environment consistent with the marine environment in the isolation and culture chamber, so as to ensure that the enriched deep-sea microorganisms are separated and cultured under the in-situ environmental conditions; the environmental parameter detection unit is used for real-time detection of temperature and pressure changes in the isolation and culture chamber and transmission of detected data to the central control system; and the microorganism isolation branch and the liquid injection unit are electrically connected to the central control system.

The microorganism isolation branch includes a removable reservoir, a pellet, a reciprocating puller, a guide chute, and a cavity; the removable reservoir is disposed in a center of a top of the cavity, and located under the central liquid injection pipe for storing the marine microorganism enrichment bacteria liquid injected by the liquid injection unit; the pellet is placed in the removable reservoir and submerged by the injected marine microorganism enrichment bacteria liquid; a through hole is provided in a bottom of the removable reservoir for fixing a position of the pellet and ensuring that the pellet is able to pass through the through hole; a movable end of the reciprocating puller is fixedly connected to the removable reservoir; a stop box is disposed on a side face of the top of the cavity; a control end of the reciprocating puller is electrically connected to the central control system; the guide chute is fixedly disposed inside the cavity; the guide chute is filled with a culture medium, and an inlet of the guide chute communicates with the stop box; after the pellet is submerged in the marine microorganism enrichment bacteria liquid, the removable reservoir moves toward an edge of the cavity under action of the reciprocating puller; when the through hole of the removable reservoir leaves the cavity, the pellet passes through the through hole and falls into the stop box of the cavity due to gravity, and enters the guide chute inside the cavity; and while the pellet carries the marine microorganism enrichment bacteria liquid to slide along the guide chute from top to bottom, the marine microorganism enrichment bacteria liquid is dispersed through concentration gradient dilution to provide a maximum area for isolation and culture of the microorganisms.

A small slot is provided in the center of the top of the cavity, that is, a position where an initial position of the removable reservoir coincides with the through hole, for fixing the position of the pellet.

The liquid injection unit includes the microinjection pump and a liquid injection pipeline; a liquid inlet end of the microinjection pump is connected to the last microbial liquid enrichment culture chamber of the enrichment and multistage purification unit, and a liquid outlet end of the microinjection pump is connected to the liquid injection pipeline; a liquid outlet of the liquid injection pipeline is connected to the central liquid injection pipe; and a control end of the microinjection pump is electrically connected to the central control system.

The environmental parameter detection unit includes a second temperature sensor and a second pressure sensor, probes of the second temperature sensor and the second pressure sensor are disposed inside the isolation and culture chamber, and signal output ends of the second temperature sensor and the second pressure sensor are electrically connected to the central control system.

In the above-mentioned solution, the temperature and pressure in the microbial liquid enrichment culture chambers and the isolation and culture chamber are monitored in real time through the temperature sensors, the pressure sensors, the second temperature sensor and the second pressure sensor respectively. If the temperature/pressure needs to be regulated, the temperature controlling system and the pressure control system are controlled by the central control system to operate and keep the temperature and pressure values in the microbial liquid enrichment culture chambers and the isolation and culture chamber consistent with the marine environmental conditions for microbial growth at all times.

A quick-open kettle lid is disposed on the top of the isolation and culture chamber, and the central liquid injection pipe is disposed on the quick-open kettle lid; the quick-open kettle lid is further provided with a gas injection channel and a sensor containing channel; the pressure control system is connected to the isolation and culture chamber through the gas injection channel; and the second temperature sensor and the second pressure sensor are disposed in the sensor containing channel.

In the above-mentioned solution, the isolation and culture chamber adopts the principle of natural release under gravity, and the pellet carries the bacteria liquid to move freely in the isolation and culture chamber under the action of gravity, such that effective isolation of the microorganisms on the solid culture medium is achieved. Samples may be quickly fed into the culture chamber through the quick-open kettle lid designed on the top of the isolation and culture chamber. For effective space utilization, this solution adopts a circular truncated cone-shaped or cylindrical cavity, which maximizes an area for microbial isolation and culture in a limited space. The rotating serpentine guide chute is disposed inside the cavity from top to bottom, and the guide chute is flatly filled with the solid culture medium for culturing the substrate, so as to provide nutritions for microorganism isolation and culture. In this solution, the removable reservoir is placed on the top of the circular truncated cone-shaped/cylindrical cavity for storing a microbial enrichment liquid to be isolated and the pellet. A diameter of the guide chute is larger than that of the pellet, thus ensuring that the pellet released from the removable reservoir may enter the guide chute completely and smoothly. The central liquid injection pipe is disposed in the center of the quick-open kettle lid for injecting the microbial enrichment liquid into the removable reservoir. The hole with a diameter slightly larger than that of the pellet is provided in a center of the bottom of the removable reservoir. The reciprocating puller is disposed on a side wall of the isolation and culture chamber, and the puller may achieve reciprocating sliding through a reciprocating piston and other control methods. The reciprocating puller may be used for dragging the removable reservoir from the center of the cavity to the edge, and since the diameter of the hole in the center of the bottom of the removable reservoir is larger than that of the pellet, the pellet may be released from the hole in the center of the bottom of the removable reservoir, enters the guide chute, then spirals down from top to bottom in the guide chute under the action of gravity, and moves to a bottom of the cavity. In the movement process of the pellet, the microbial enrichment liquid is dispersed in the guide chute through concentration gradient dilution to meet the requirements for dispersion growth of a single colony.

Preferably, a plurality of isolation and culture chambers are disposed in sequence, and the liquid injection unit is connected to the central liquid injection pipes of all the isolation and culture chambers; the temperature controlling system and the pressure control system are connected to all the isolation and culture chambers respectively for constructing the high-pressure and low-temperature environment consistent with the marine environment in each of the isolation and culture chambers, so as to ensure that the enriched deep-sea microorganisms are isolated and cultured under the in-situ environmental conditions; and each of the isolation and culture chambers is connected to an independent environmental parameter detection unit for real-time monitoring of temperature and pressure changes in the isolation and culture chamber and transmission of detected data to the central control system.

A microorganism isolation process involved in this solution is mainly a process in which the plurality of isolation and culture chambers are placed in parallel, and inlets of all the isolation and culture chambers are connected in parallel by piping and connected to the microinjection pump and the last microbial liquid enrichment culture chamber. In order to facilitate selection of an optimal culture method, culture media of different formulations may be placed in different culture chambers.

The pressure control system includes a bleed valve, an air compressor, a booster pump, a gas storage tank, a pressure regulating valve, a regulating valve, and a vent pipeline; the bleed valve is connected to the enrichment and multistage purification unit and the gravity-type isolation and culture unit through the vent pipeline, and a control end of the bleed valve is electrically connected to the central control system for discharging gas from the enrichment and multistage purification unit and the gravity-type isolation and culture unit, and for depressurizing interior of the enrichment and multistage purification unit and the gravity-type isolation and culture unit; the air compressor, the booster pump, the gas storage tank, the pressure regulating valve and the regulating valve are connected in sequence through the vent pipeline, and finally connected to the enrichment and multistage purification unit and the gravity-type isolation and culture unit through the vent pipeline for filling the enrichment and multistage purification unit and the gravity-type isolation and culture unit with gas (or inert gas) required for culture for pressurization; the pressure regulating valve is used for regulating internal pressure of the enrichment and multistage purification unit and the gravity-type isolation and culture unit; the regulating valve is used for regulating a speed of gas injection; and a control end of the air compressor, a control end of the booster pump, a control end of the pressure regulating valve, and a control end of the regulating valve are electrically connected to the central control system.

The temperature controlling system includes a water bath jacket and a refrigerating/heating device; the water bath jacket is wrapped on outer walls of the enrichment and multistage purification unit and the gravity-type isolation and culture unit, and is connected to the refrigerating/heating device; and a control end of the refrigerating/heating device is electrically connected to the central control system.

In the above-mentioned solution, constant temperature conditions in the microbial liquid enrichment culture chambers and the isolation and culture chamber are maintained mainly by placing the microbial liquid enrichment culture chambers and the isolation and culture chamber in a high/low-temperature water bath of the water bath jacket, and the constant-temperature state in the culture chambers is maintained by carrying out monitoring and displaying through the temperature sensors and the second temperature sensor, and carrying out heat exchange with the refrigerating/heating device.

In the above-mentioned solution, the temperature conditions of the microbial liquid enrichment culture chambers and the isolation and culture chamber are mainly controlled through the temperature controlling system. For example, a refrigerating/heating fluid is injected into an annular wall cavity of the microbial liquid enrichment culture chambers and the isolation and culture chamber, a low-temperature or high-temperature state of the fluid in the annular wall cavity is ensured through circulating refrigeration or heating of the fluid, and then a low-temperature or high-temperature state in an internal cavity is ensured through heat exchange between the refrigerating/heating fluid and the internal cavity. Alternatively, the microbial liquid enrichment culture chambers and the isolation and culture chamber are placed in a low temperature/high temperature water bath/oil bath environment to ensure special temperature conditions required within the microbial liquid enrichment culture chambers and the isolation and culture chamber. Alternatively, the microbial liquid enrichment culture chambers and the isolation and culture chamber are placed in a refrigerating/heating room or box with constant temperature ensured by air heat exchange. Some extreme temperature conditions may be maintained by using the above temperature control methods at the same time.

The device for enrichment culture and gravity-type isolation of the marine microorganisms in the high-pressure environment further includes a mobile platform, and the enrichment and multistage purification unit, the gravity-type isolation and culture unit, the temperature controlling system, the pressure control system, and the central control system are placed on the mobile platform for improving general applicability to a culture scenario.

In the above-mentioned solution, the survival activity of the microorganisms is improved by constructing the high-pressure and extreme temperature environmental conditions under which the microorganisms live in the marine environment in the microbial liquid enrichment culture chambers and the isolation and culture chamber. Functional microorganisms with higher purity under stress of targeted environmental conditions are obtained through multistage enrichment and liquid dilution culture, and single microorganisms are obtained by culture and isolation in combination with the isolation and culture chamber. At the same time, an efficient isolation process with different culture medium combinations may be formed by selectively combining the microbial liquid enrichment culture chambers and isolation and culture chamber.

Technology for enrichment culture and isolation of the marine microorganisms in the high-pressure environment involved in the device provided by this solution mainly includes two steps: enrichment and isolation. First, after enrichment culture by the enrichment and multistage purification unit, a bacteria group with higher purity is obtained, and enters the gravity-type isolation and culture unit under a pressure-holding condition for solid culture and isolation, and a pure culture strain is obtained by screening at the same time by a combination process of different culture media and environmental conditions. A specific implementation principle is as follows.

Enrichment: the microbial liquid enrichment culture chambers and attached pipe valve members thereof are first sterilized, then substrates to be cultured, such as deep sea sediments, macro-biological tissues symbiotic with the microorganisms, and an extracting solution, are fed in sequence, then a nutrient solution required for culture is fed from the liquid inlet valves, and then gas (inert gas may be injected if gas is not required) required for culture is injected from the gas inlet valves, such that the pressure values in the microbial liquid enrichment culture chambers are increased to be consistent with the actual environmental conditions in the deep sea. In the culture process, the manual stirring rods on the top are used for stirring to enhance a mass transfer effect and optimize the culture process. After the culture process in a first microbial liquid enrichment culture chamber is completed, a nutrient solution required for culture is injected into a second microbial liquid enrichment culture chamber, and gas is injected into the second microbial liquid enrichment culture chamber through the pressure control system for pressurization. The amount of the culture solution injected into the second microbial liquid enrichment culture chamber needs to ensure that a dilution ratio of the concentration of an enrichment liquid from the first microbial liquid enrichment culture chamber to the second microbial liquid enrichment culture chamber meets purification requirements, and then the microbial bacteria liquid in the first microbial liquid enrichment culture chamber is transferred to the second microbial liquid enrichment culture chamber through pressure-holding transfer. On this basis, the microorganisms in the last microbial liquid enrichment culture chamber may reach a highly purified state. When the concentration of the deep-sea microbial bacteria liquid in the last microbial liquid enrichment culture chamber reaches $10^6$ cfu/mL or more, it may be considered that a desirable purification state is achieved. The dilution ratio at each stage may be regulated for a particular cultured microbial group.

After it is identified that the bacteria liquid concentration in the enrichment process meets the requirements, the isolation and culture process is started.

Isolation: first, the isolation and culture chamber and all internal components and associated pipe valve members thereof are sterilized to maintain a sterile state. The guide chute in the surface of the microorganism isolation branch is then filled with a culture medium required for culture, the microorganism isolation branch is installed in the cavity, and the removable reservoir is placed on the top of the microorganism isolation branch. The reciprocating puller is then installed. The quick-open kettle lid of the culture chamber is then installed to ensure that the central liquid injection pipe is unblocked. Then gas is injected into the isolation and culture chambers through the pressure control system for pressurization, such that the pressure conditions in the isolation and culture chambers are consistent with the pressure conditions in the microbial liquid enrichment culture chambers. After ensuring normal operation of all system components, the microinjection pump is started to inject a small amount of marine microorganism enrichment bacteria liquid into the removable reservoir on the microorganism isolation branch from the last microbial liquid enrichment culture chamber through the central liquid injection pipe, such that the marine microorganism enrichment bacteria liquid is uniformly dispersed on the pellet. Then, the reciprocating puller is started to drag the removable reservoir at the stop box of the guide chute on the side face of the circular truncated cone. Since the diameter of the pellet is smaller than the diameter of the hole in the bottom of the removable reservoir, the pellet may be released from the removable reservoir into the guide chute, and may spiral from top to bottom in the guide chute and move to the bottom under the action of gravity. The enriched bacteria liquid on the pellet may be dispersed in the guide chute to meet the isolation and purification culture process. Along a trajectory of movement of the pellet, a streaking trajectory of the bacteria liquid may be gradient dilution, and isolated colonies may grow along a guide trajectory. At this moment, the isolation process is completed.

This solution further relates to an automatic microorganism isolation process, which is mainly a process in which the plurality of isolation and culture chambers are placed in parallel, and inlets of all the isolation and culture chambers are connected in parallel by piping and connected to the microinjection pump and the last microbial liquid enrichment culture chamber. In order to facilitate selection of an optimal culture method, culture media of different formulations may be placed in different culture chambers. All the isolation and culture chambers and pipe valve members involved in the culture process are then integrally sterilized, and then whether microorganism isolation branches, pellets, reciprocating pullers, guide chutes, central liquid injection pipes, and accessory systems thereof in all the culture chambers are properly installed is checked. Then, by monitoring the temperature and pressure, it is ensured that the temperature and pressure environmental conditions in all the isolation and culture chambers are consistent with the temperature and pressure environmental conditions of the marine environment in which the microorganisms are located. The microinjection pumps, the regulating valves, the central liquid injection pipes, and the reciprocating pullers are started in sequence, and the pellets may carry the bacteria liquid to move in the guide chute of the microorganism isolation branch in each of the isolation and culture chambers. By automatic separation and combination of a large number of culture chambers, an automatic isolation process in different culture medium environments may be achieved, thereby effectively ensuring isolation, culture and purification of the microorganisms in the high-pressure environment, and providing a key technology for efficient utilization of the marine microorganisms and a sorting process in the high-pressure environment. Data acquisition, integration and display of parameter conditions in the whole culture process may be carried out through the central control system.

This solution relates to the device and process for enrichment culture and gravity-type isolation of the marine microorganisms in the high-pressure environment, proposes multistage enrichment culture and multi-culture medium automatic isolation and purification culture of the marine microorganisms under the high-pressure and extreme temperature environmental conditions, and solves the problem that a large number of microorganisms cannot be purely cultured because existing indoor pure culture technology and method are detached from the high-pressure and extreme temperature environmental conditions where the marine microorganism live. This solution does not require professional operators, can be used in research laboratories, research vessels and other culture scenarios, and has high adaptability. This solution does not require professional personnel to perform manual enrichment and streaking isolation, and can perform large-scale enrichment and sorting, thereby reducing labor costs, realizing automatic isolation and culture of the marine microorganisms under in-situ pressure and temperature environmental conditions, and providing an important technical means for pure culture of the marine microorganisms under in-situ conditions.

Compared with the existing pure culture technology, this solution proposes high-pressure pure culture technology for enrichment and isolation and culture of the marine microorganisms under the marine in-situ high-pressure and extreme temperature environmental conditions, which solves the problem that most microorganisms cannot be isolated and purely cultured because the existing atmospheric pressure isolation and culture technology is detached from the temperature and pressure environmental conditions in which the marine microorganisms live in situ. Compared with the existing isolation and culture technology, this solution can effectively reduce the input of professional personnel, and can perform large-scale enrichment and isolation and culture, thereby improving the screening efficiency of difficult-to-culture microorganisms, and improving the screening and cultivation efficiency of engineering bacteria with special functions.

Compared with the prior art, the technical solution of the present invention has the following beneficial effects.

The present invention provides the device for enrichment culture and gravity-type isolation of the marine microorganisms in the high-pressure environment, enrichment culture of the microorganisms under the marine in-situ temperature and pressure environmental conditions is achieved through the enrichment and multistage purification unit, and isolation and culture of the marine microorganisms are achieved through the gravity-type isolation and culture unit. By reconstructing the in-situ environment for enrichment culture and isolation of the marine microorganisms, the problem about isolation and pure culture of the marine microorganisms in the high-pressure environment is solved, the culturability of the marine microorganisms is effectively improved, and an important basic means is provided for development and utilization of deep-sea microorganism resources.

1 denotes an enrichment and multistage purification unit; 11 denotes a microbial liquid enrichment culture chamber; 111 denotes a removal sealing lid; 112 denotes a sensor set; 1121 denotes a temperature sensor; 1122 denotes a pressure sensor; 113 denotes a stirring rod; 1141 denotes a liquid inlet valve; 1142 denotes a gas inlet valve; 1143 denotes a sampling valve; 1144 denotes a liquid outlet valve; 2 denotes a gravity-type isolation and culture unit; 21 denotes an isolation and culture chamber; 211 denotes a microorganism isolation branch; 2111 denotes a removable reservoir; 2112 denotes a pellet; 2113 denotes a reciprocating puller; 2114 denotes a guide chute; 2115 denotes a cavity; 2116 denotes a stop box; 212 denotes a central liquid injection pipe; 213 denotes a quick-open kettle lid; 22 denotes a liquid injection unit; 221 denotes a microinjection pump; 222 denotes a liquid injection pipeline; 23 denotes an environmental parameter detection unit; 231 denotes a second temperature sensor; 232 denotes a second pressure sensor; 3 denotes a temperature controlling system; 31 denotes a water bath jacket; 32 denotes a refrigerating/heating device; 33 denotes a water bath temperature detection device; 4 denotes a pressure control system; 41 denotes a bleed valve; 42 denotes an air compressor; 43 denotes a booster pump; 44 denotes a gas storage tank; 45 denotes a pressure regulating valve; 46 denotes a regulating valve; 47 denotes a vent pipeline; 5 denotes a central control system; and 6 denotes a mobile platform.

DETAILED DESCRIPTION

The accompanying drawings are for illustrative purposes merely and should not be construed as limitations on this patent.

The following examples are complete use examples with rich contents.

In order to better illustrate the examples, some parts in the accompanying drawings are omitted, enlarged, or reduced, and do not represent the size of actual products.

It may be understood by those skilled in the art that some well-known structures and descriptions thereof may be omitted from the accompanying drawings.

The technical solutions of the present invention are further described below in conjunction with the accompanying drawings and examples.

Example 1

Figure 1:
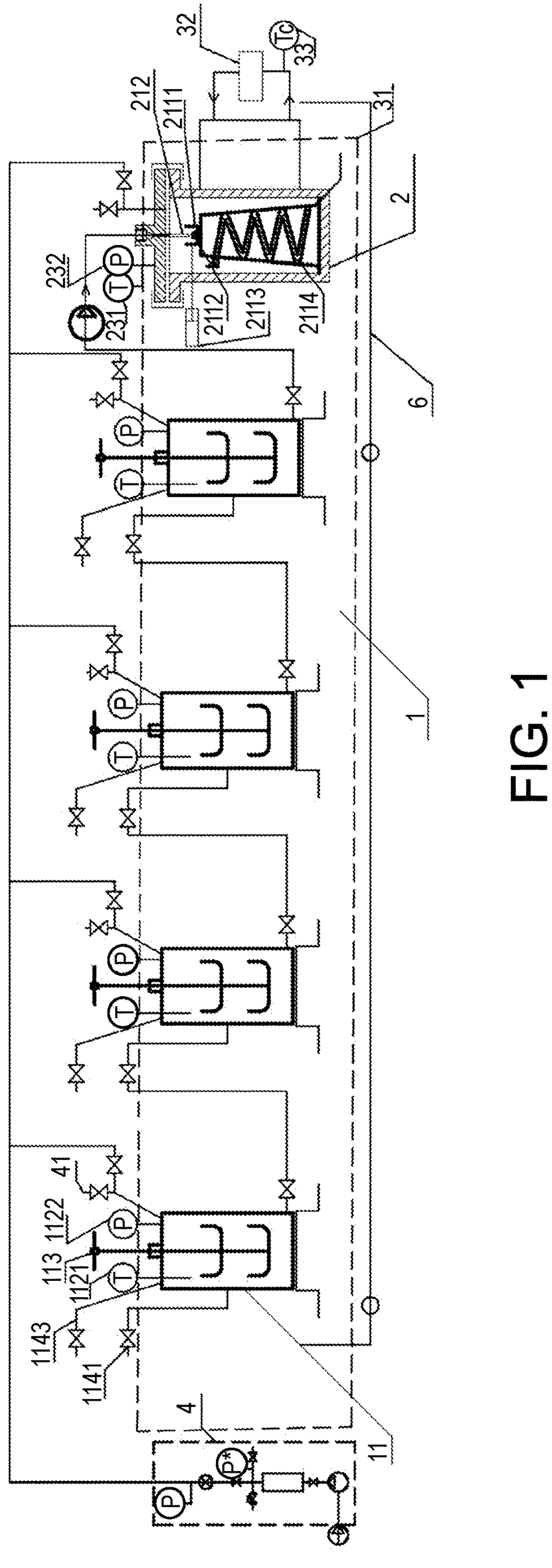
FIG. 1 is a schematic structural diagram of a device according to the present invention.

As shown in FIG. 1, this solution provides a device for enrichment culture and gravity-type isolation of marine microorganisms in a high-pressure environment. The device includes an enrichment and multistage purification unit 1, a gravity-type isolation and culture unit 2, a temperature controlling system 3, a pressure control system 4, and a central control system 5. Control ends and signal detection ends of the enrichment and multistage purification unit 1 and the gravity-type isolation and culture unit 2 are electrically connected to the central control system 5. Control ends of the temperature controlling system 3 and the pressure control system 4 are electrically connected to the central control system 5. The enrichment and multistage purification unit 1 is used for realizing a process of enrichment and multistage purification of the marine microorganisms, obtaining a marine microorganism enrichment bacteria liquid, and injecting the marine microorganism enrichment bacteria liquid to the gravity-type isolation and culture unit 2. The gravity-type isolation and culture unit 2 are used for carrying out automatic streaking by means of gravity in the high-pressure environment to achieve solid isolation and culture of the marine microorganisms, such that culturability of the marine microorganisms is effectively improved. The temperature controlling system 3 and the pressure control system 4 are connected to the enrichment and multistage purification unit 1 and the gravity-type isolation and culture unit 2 respectively for constructing a high-pressure and low-temperature environment consistent with a marine environment in the enrichment and multistage purification unit 1 and the gravity-type isolation and culture unit 2, so as to ensure that enriched deep-sea microorganisms are enriched, purified, separated and cultured under in-situ environmental conditions.

In a specific implementation process, the enrichment and multistage purification unit 1 may achieve enrichment culture of the microorganisms under marine in-situ temperature and pressure environmental conditions, and the gravity-type isolation and culture unit 2 may achieve isolation and culture of the marine microorganisms. By reconstructing the in-situ environment for enrichment culture and isolation of the marine microorganisms, the problem about isolation and pure culture of the marine microorganisms in the high-pressure environment is solved, the culturability of the marine microorganisms is effectively improved, and an important basic means is provided for development and utilization of deep-sea microorganism resources.

In a specific implementation process, the central control system 5 is used for realizing monitoring of changes of various environmental data information, as well as real-time acquisition, processing, storage, image output, and other functions during enrichment, isolation and purification of microbial enrichment bacteria in the high-pressure environment.

Figure 2:
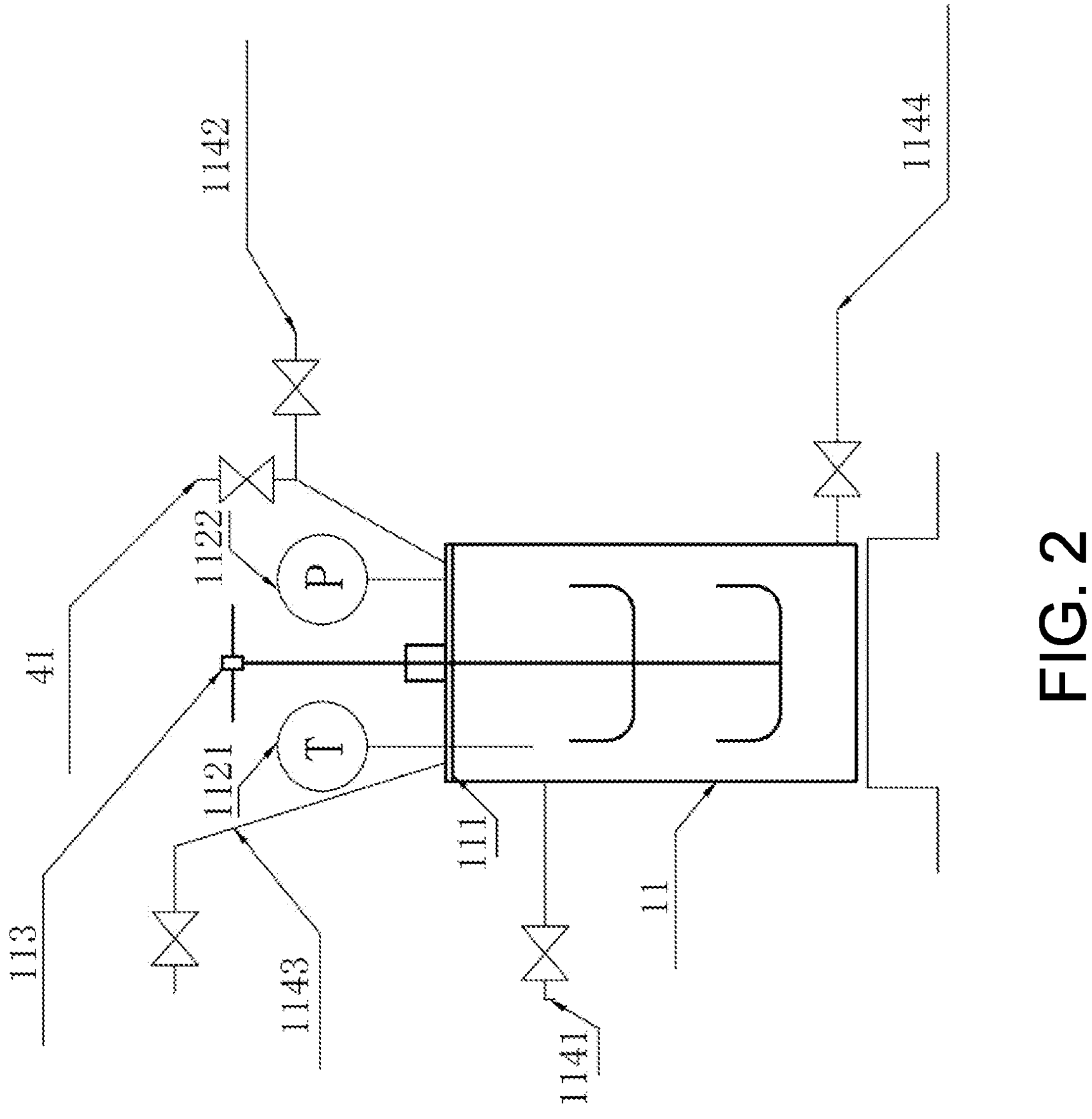
FIG. 2 is a schematic structural diagram of a microbial liquid enrichment culture chamber according to the present invention.
Figure 4:
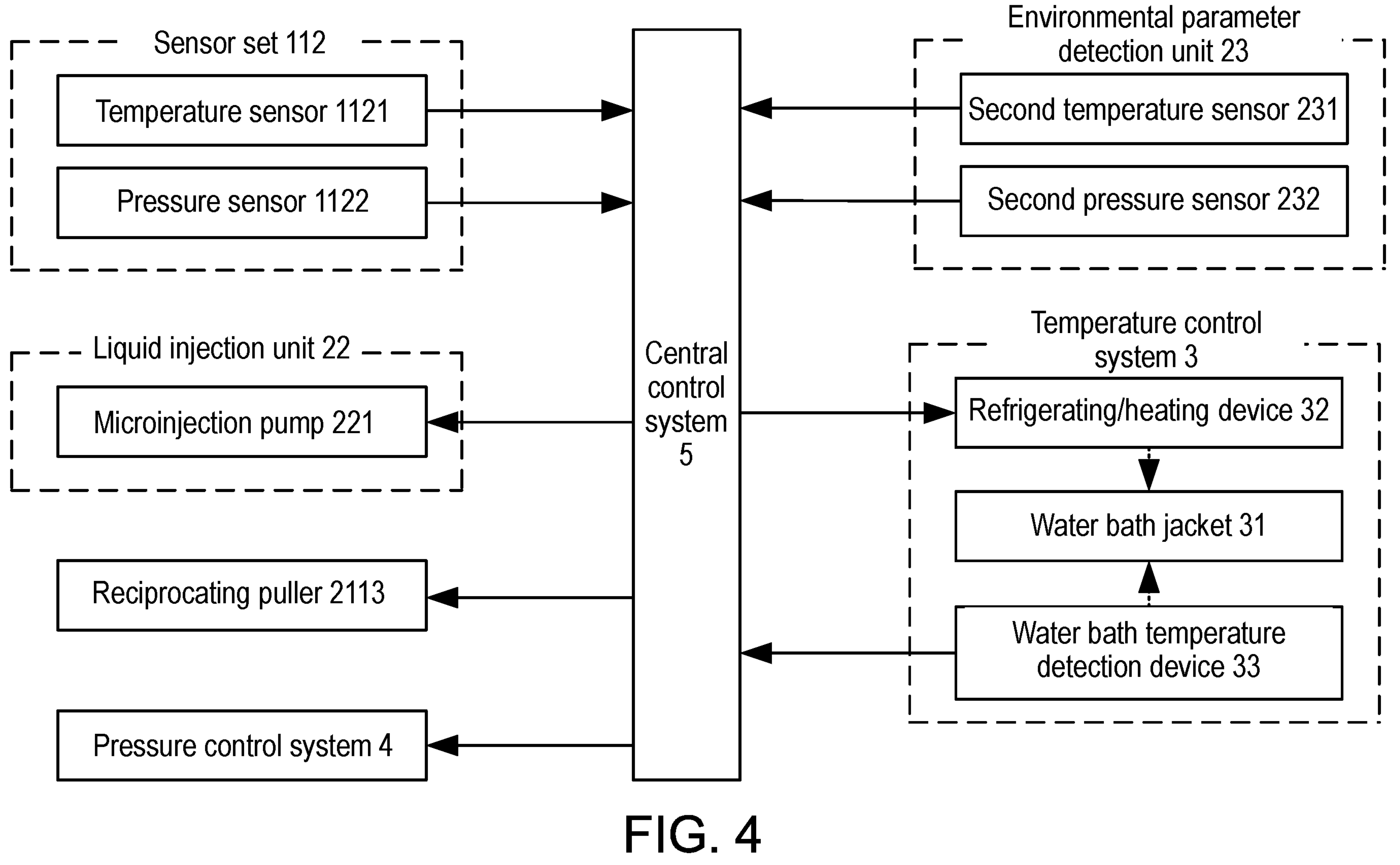
FIG. 4 is a schematic diagram of connection of circuit modules of a central control system according to the present invention.

More specifically, as shown in FIG. 1, FIG. 2 and FIG. 4, the enrichment and multistage purification unit 1 includes a plurality of microbial liquid enrichment culture chambers 11 connected in series. The microbial liquid enrichment culture chambers 11 are provided with removable sealing lids 111 and connection and sampling valve sets, and sensor sets 112 are disposed inside the microbial liquid enrichment culture chambers. Each of the microbial liquid enrichment culture chambers 11 is disposed in the temperature controlling system 3. The removable sealing lids 111 are used for facilitating sterilization operations and placement of culture substrates inside the microbial liquid enrichment culture chambers 11. The connection and sampling valve sets are used for connection and sampling of the microbial liquid enrichment culture chambers 11, and are connected to the pressure control system 4 for feeding liquid or gas into the microbial liquid enrichment culture chambers 11 to increase pressure inside the microbial liquid enrichment culture chambers 11, so as to ensure that pressure values in the microbial liquid enrichment culture chambers 11 are consistent with actual conditions in a deep sea. The sensor sets 112 are used for real-time monitoring of temperature and pressure changes in the microbial liquid enrichment culture chambers 11, and transmitting signals to the central control system 5. A last microbial liquid enrichment culture chamber 11 of the enrichment and multistage purification unit 1 is connected to the gravity-type isolation and culture unit 2 through a connection and sampling valve set.

More specifically, the microbial liquid enrichment culture chambers 11 are further provided with stirring rods 113, and the stirring rods 113 are used for enhancing a reaction process of a substrate in a culture process of the microbial liquid enrichment culture chambers 11.

In a specific implementation process, the stirring rods 113 are manual stirring rods, and may enhance mass transfer through intermittent manual stirring, or enhanced continuous or intermittent stirring rods 113 may be placed as needed for enhancing the reaction process of the substrate in the culture process, thereby increasing energy and nutrient supply to the microorganisms and improving culture efficiency.

The sensor sets 112 include temperature sensors 1121 and pressure sensors 1122. The temperature sensors 1121 are used for real-time monitoring of temperature changes in the microbial liquid enrichment culture chambers 11. The pressure sensors 1122 are used for real-time monitoring of pressure changes in the microbial liquid enrichment culture chambers 11. Signal output ends of the temperature sensors 1121 and signal output ends of the pressure sensors 1122 are electrically connected to the central control system 5.

More specifically, the connection and sampling valve sets include liquid inlet valves 1141, gas inlet valves 1142, sampling valves 1143, and liquid outlet valves 1144. The microbial liquid enrichment culture chambers 11 are connected in series through the liquid outlet valves 1144 and the liquid inlet valves 1141, and a liquid outlet valve 1144 of a former microbial liquid enrichment culture chamber 11 is connected to a liquid inlet valves 1141 of a latter microbial liquid enrichment culture chamber 11. A liquid outlet valve 1144 of the last microbial liquid enrichment culture chamber 11 is connected to the gravity-type isolation and culture unit 2. The gas inlet valves 1142 are connected to the pressure control system 4 for feeding gas into the microbial liquid enrichment culture chambers 11 to increase the pressure in the microbial liquid enrichment culture chambers 11, such that the pressure values in the microbial liquid enrichment culture chambers 11 are consistent with the actual conditions in the deep sea. The sampling valves 1143 are used for real-time sampling and analysis of the microorganisms in the microbial liquid enrichment culture chambers 11.

In a specific implementation process, the plurality of microbial liquid enrichment culture chambers 11 are connected in series to form the enrichment and multistage purification unit 1, a bacteria liquid in the former microbial liquid enrichment culture chamber 11 enters the next microbial liquid enrichment culture chamber 11 through pressure-holding transfer. On this basis, through concentration gradient dilution, a microbial bacteria liquid obtained in the last microbial liquid enrichment culture chamber 11 may be functional microorganisms enriched and highly purified in a high-pressure environment and under supply stress of directed nutrient conditions. Pressure-holding transfer may be achieved by sampling the enrichment liquid from the former microbial liquid enrichment culture chamber 11 by a microinjection pump through the sampling valves 1143 and then pumping the enrichment liquid into the latter microbial liquid enrichment culture chamber 11. Pressure of the latter microbial liquid enrichment culture chamber 11 may be increased to be slightly smaller than pressure of the former microbial liquid enrichment culture chamber 11, then the liquid outlet valve 1144 of the former microbial liquid enrichment culture chamber 11 and the liquid inlet valve 1141 of the latter microbial liquid enrichment culture chamber are opened, and the microbial enrichment liquid may automatically enter the latter microbial liquid enrichment culture chamber 11 from the former microbial liquid enrichment culture chamber 11 for dilution culture under the condition of a small pressure difference. In the whole enrichment culture process, the temperature and pressure environmental conditions in the microbial liquid enrichment culture chambers 11 are consistent with the environmental conditions of the microorganisms in the deep sea to ensure validity of enrichment culture.

Figure 3:
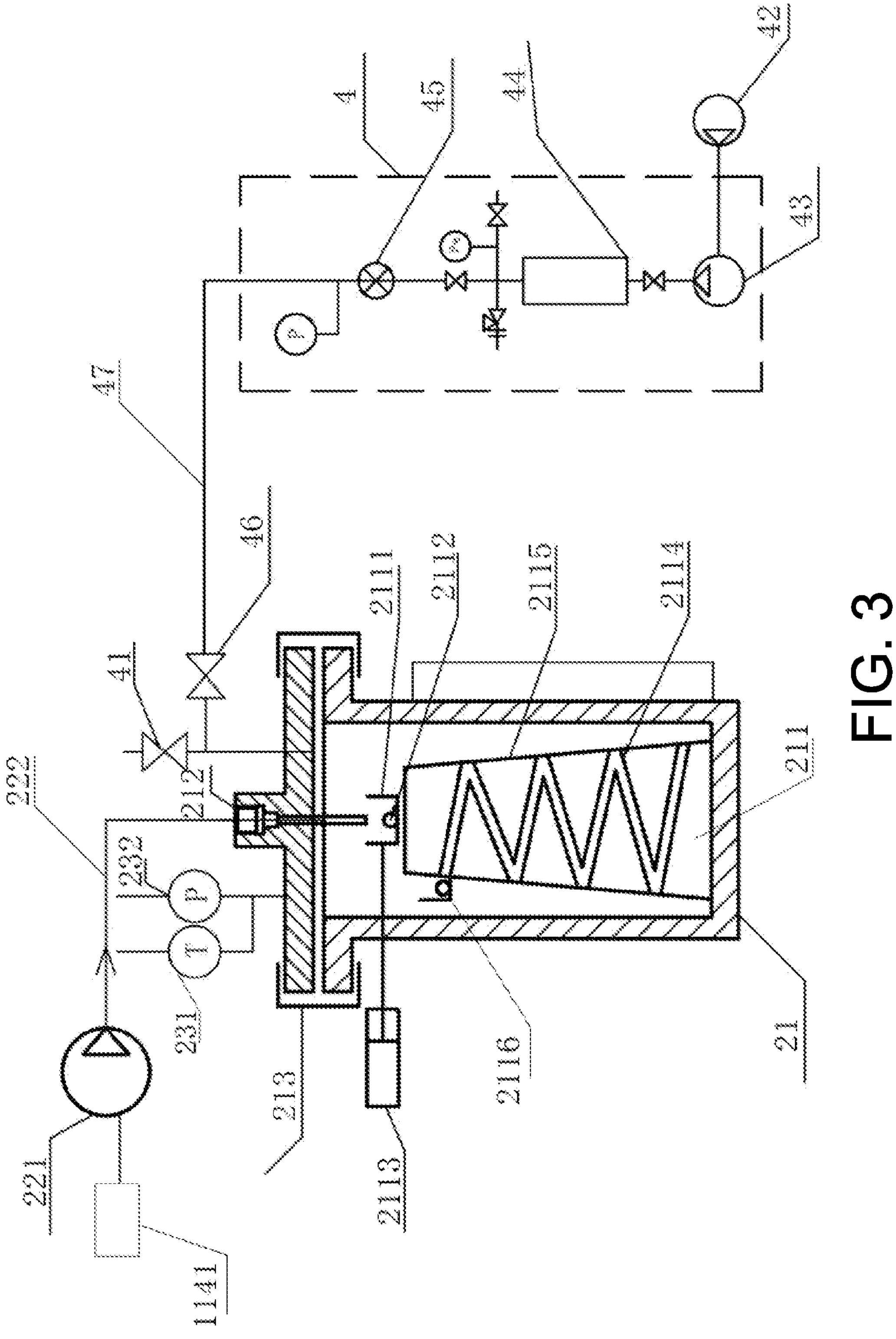
FIG. 3 is a schematic structural diagram of an isolation and culture chamber and a pressure control system according to the present invention.

More specifically, as shown in FIG. 1, FIG. 3 and FIG. 4, the gravity-type isolation and culture unit 2 includes an isolation and culture chamber 21, a liquid injection unit 22, and an environmental parameter detection unit 23. The gravity-type isolation and culture unit 2 is connected to the last microbial liquid enrichment culture chamber 11 of the enrichment and multistage purification unit 1 through the liquid injection unit 22. A microorganism isolation branch 211 is disposed in the isolation and culture chamber 21 for carrying out an isolation operation on microorganisms to provide a maximum area for microorganism culture. A central liquid injection pipe 212 is disposed on a top of the isolation and culture chamber 21, and the isolation and culture chamber 21 is connected to the liquid injection unit 22 through the central liquid injection pipe 212. A marine microorganism enrichment bacteria liquid is injected by the liquid injection unit 22 into the microorganism isolation branch 211 of the isolation and culture chamber 21. The isolation and culture chamber 21 is disposed in the temperature controlling system 3 and connected to the pressure control system 4 for constructing the high-pressure and low-temperature environment consistent with the marine environment in the isolation and culture chamber 21 to ensure that the enriched deep-sea microorganisms are isolated and cultured under the in-situ environmental conditions. The environmental parameter detection unit 23 is used for real-time detection of temperature and pressure changes in the isolation and culture chamber 21 and transmission of detected data to the central control system 5. The microorganism isolation branch 211 and the liquid injection unit 22 are electrically connected to the central control system 5.

More specifically, the microorganism isolation branch 211 includes a removable reservoir 2111, a pellet 2112, a reciprocating puller 2113, a guide chute 2114, and a cavity 2115.

The removable reservoir 2111 is disposed in a center of a top of the cavity 2115, and located under the central liquid injection pipe 212 for storing the marine microorganism enrichment bacteria liquid injected by the liquid injection unit 22. The pellet 2112 is placed in the removable reservoir 2111 and submerged by the injected marine microorganism enrichment bacteria liquid. A through hole is provided in a bottom of the removable reservoir 2111 for fixing a position of the pellet 2112 and ensuring that the pellet 2112 is able to pass through the through hole. A movable end of the reciprocating puller 2113 is fixedly connected to the removable reservoir 2111. A stop box 2116 is disposed on a side face of the top of the cavity 2115. A control end of the reciprocating puller 2113 is electrically connected to the central control system 5. The guide chute 2114 is fixedly disposed inside the cavity 2115. The guide chute 2114 is filled with a culture medium, and an inlet of the guide chute communicates with the stop box 2116. After the pellet 2112 is submerged in the marine microorganism enrichment bacteria liquid, the removable reservoir 2111 moves toward an edge of the cavity 2115 under action of the reciprocating puller 2113. When the through hole of the removable reservoir 2111 leaves the cavity 2115, the pellet 2112 passes through the through hole and falls into the stop box 2116 of the cavity 2115 due to gravity, and enters the guide chute 2114 inside the cavity 2115. While the pellet 2112 carries the marine microorganism enrichment bacteria liquid to slide along the guide chute 2114 from top to bottom, the marine microorganism enrichment bacteria liquid is dispersed through concentration gradient dilution to provide a maximum area for isolation and culture of the microorganisms.

More specifically, a small slot is provided in the center of the top of the cavity 2115, that is, a position where an initial position of the removable reservoir 2111 coincides with the through hole, for fixing the position of the pellet 2112.

More specifically, the liquid injection unit 22 includes the microinjection pump 221 and a liquid injection pipeline 222. A liquid inlet end of the microinjection pump 221 is connected to the last microbial liquid enrichment culture chamber 11 of the enrichment and multistage purification unit 1, and a liquid outlet end of the microinjection pump is connected to the liquid injection pipeline 222. A liquid outlet of the liquid injection pipeline 222 is connected to the central liquid injection pipe 212. A control end of the microinjection pump 221 is electrically connected to the central control system 5.

More specifically, the environmental parameter detection unit 23 includes a second temperature sensor 231 and a second pressure sensor 232. Probes of the second temperature sensor 231 and the second pressure sensor 232 are disposed inside the isolation and culture chamber 21, and signal output ends of the second temperature sensor and the second pressure sensor are electrically connected to the central control system 5.

In a specific implementation process, the temperature and pressure in the microbial liquid enrichment culture chambers 11 and the isolation and culture chamber 21 are monitored in real time through the temperature sensors 1121, the pressure sensors 1122, the second temperature sensor 231 and the second pressure sensor 232 respectively. If the temperature/pressure needs to be regulated, the temperature controlling system 3 and the pressure control system 4 are controlled by the central control system 5 to operate and keep the temperature and pressure values in the microbial liquid enrichment culture chambers and the isolation and culture chamber consistent with the marine environmental conditions for microbial growth at all times.

More specifically, a quick-open kettle lid 213 is disposed on the top of the isolation and culture chamber 21, and the central liquid injection pipe 212 is disposed on the quick-open kettle lid 213. The quick-open kettle lid 213 is further provided with a gas injection channel and a sensor containing channel. The pressure control system 4 is connected to the isolation and culture chamber 21 through the gas injection channel. The second temperature sensor 231 and the second pressure sensor 232 are disposed in the sensor containing channel.

In a specific implementation process, the isolation and culture chamber 21 adopts the principle of natural release under gravity, and the pellet 2112 carries the bacteria liquid to move freely in the isolation and culture chamber 21 under the action of gravity, such that effective isolation of the microorganisms on the solid culture medium is achieved. Samples may be quickly fed into the culture chamber through the quick-open kettle lid 213 designed on the top of the isolation and culture chamber 21. For effective space utilization, this example adopts a circular truncated cone-shaped or cylindrical cavity 2115, which maximizes an area for microbial isolation and culture in a limited space. The rotating serpentine guide chute 2114 is disposed inside the cavity 2115 from top to bottom, and the guide chute 2114 is flatly filled with the solid culture medium for culturing the substrate, so as to provide nutritions for microorganism isolation and culture. In this example, the removable reservoir 2111 is placed on the top of the circular truncated cone-shaped/cylindrical cavity 2115 for storing a microbial enrichment liquid to be isolated and the pellet 2112. A diameter of the guide chute 2114 is larger than that of the pellet 2112, thus ensuring that the pellet 2112 released from the removable reservoir 2111 may enter the guide chute 2114 completely and smoothly. The central liquid injection pipe 212 is disposed in the center of the quick-open kettle lid 213 for injecting the microbial enrichment liquid into the removable reservoir 2111. The hole with a diameter slightly larger than that of the pellet 2112 is provided in a center of the bottom of the removable reservoir 2111. The reciprocating puller 2113 is disposed on a side wall of the isolation and culture chamber 21, and the puller may achieve reciprocating sliding through a reciprocating piston and other control methods. The reciprocating puller 2113 may be used for dragging the removable reservoir 2111 from the center of the cavity 2115 to the edge, and since the diameter of the hole in the center of the bottom of the removable reservoir 2111 is larger than that of the pellet 2112, the pellet 2112 may be released from the hole in the center of the bottom of the removable reservoir 2111, enters the guide chute 2114, then spirals down from top to bottom in the guide chute 2114 under the action of gravity, and moves to a bottom of the cavity 2115. In the movement process of the pellet 2112, the microbial enrichment liquid is dispersed in the guide chute 2114 through concentration gradient dilution to meet the requirements for dispersion growth of a single colony.

More specifically, the pressure control system 4 includes a bleed valve 41, an air compressor 42, a booster pump 43, a gas storage tank 44, a pressure regulating valve 45, a regulating valve 46, and a vent pipeline 47. The bleed valve 41 is connected to the enrichment and multistage purification unit 1 and the gravity-type isolation and culture unit 2 through the vent pipeline 47, and a control end of the bleed valve is electrically connected to the central control system 5 for discharging gas from the enrichment and multistage purification unit 1 and the gravity-type isolation and culture unit 2, and for depressurizing interior of the enrichment and multistage purification unit 1 and the gravity-type isolation and culture unit 2. The air compressor 42, the booster pump 43, the gas storage tank 44, the pressure regulating valve 45 and the regulating valve 46 are connected in sequence through the vent pipeline 47, and finally connected to the enrichment and multistage purification unit 1 and the gravity-type isolation and culture unit 2 through the vent pipeline 47 for filling the enrichment and multistage purification unit 1 and the gravity-type isolation and culture unit 2 with gas (or inert gas) required for culture for pressurization. The pressure regulating valve 45 is used for regulating internal pressure of the enrichment and multistage purification unit 1 and the gravity-type isolation and culture unit 2. The regulating valve 46 is used for regulating a speed of gas injection. A control end of the air compressor 42, a control end of the booster pump 43, a control end of the pressure regulating valve 45, and a control end of the regulating valve 46 are electrically connected to the central control system 5.

More specifically, the temperature controlling system 3 includes a water bath jacket 31 and a refrigerating/heating device 32. The water bath jacket 31 is wrapped on outer walls of the enrichment and multistage purification unit 1 and the gravity-type isolation and culture unit 2, and is connected to the refrigerating/heating device 32. A control end of the refrigerating/heating device 32 is electrically connected to the central control system 5.

In a specific implementation process, constant temperature conditions in the microbial liquid enrichment culture chambers 11 and the isolation and culture chamber 21 are maintained mainly by placing the microbial liquid enrichment culture chambers 11 and the isolation and culture chamber 21 in a high/low-temperature water bath of the water bath jacket 31, and the constant-temperature state in the culture chambers is maintained by carrying out monitoring and displaying through the temperature sensors 1121 and the second temperature sensor 231, and carrying out heat exchange with the refrigerating/heating device. At the same time, a water bath temperature detection device 33 is further provided, and an output end of the water bath temperature detection device is electrically connected to the central processing system 5 for detecting the water bath temperature in the water bath jacket 31 in real time, so as to facilitate real-time temperature regulation.

In a specific implementation process, the temperature conditions of the microbial liquid enrichment culture chambers 11 and the isolation and culture chamber 21 are mainly controlled through the temperature controlling system 3. For example, a refrigerating/heating fluid is injected into an annular wall cavity of the microbial liquid enrichment culture chambers 11 and the isolation and culture chamber 21, a low-temperature or high-temperature state of the fluid in the annular wall cavity is ensured through circulating refrigeration or heating of the fluid, and then a low-temperature or high-temperature state in an internal cavity is ensured through heat exchange between the refrigerating/heating fluid and the internal cavity. Alternatively, the microbial liquid enrichment culture chambers 11 and the isolation and culture chamber 21 are placed in a low temperature/high temperature water bath/oil bath environment to ensure special temperature conditions required within the microbial liquid enrichment culture chambers 11 and the isolation and culture chamber 21. Alternatively, the microbial liquid enrichment culture chambers 11 and the isolation and culture chamber 21 are placed in a refrigerating/heating room or box with constant temperature ensured by air heat exchange. Some extreme temperature conditions may be maintained by using the above temperature control methods at the same time. More specifically, the device for enrichment culture and gravity-type isolation of the marine microorganisms in the high-pressure environment further includes a mobile platform 6. The enrichment and multistage purification unit 1, the gravity-type isolation and culture unit 2, the temperature controlling system 3, the pressure control system 4, and the central control system 5 are placed on the mobile platform 6 for improving general applicability to a culture scenario.

Figure 5:
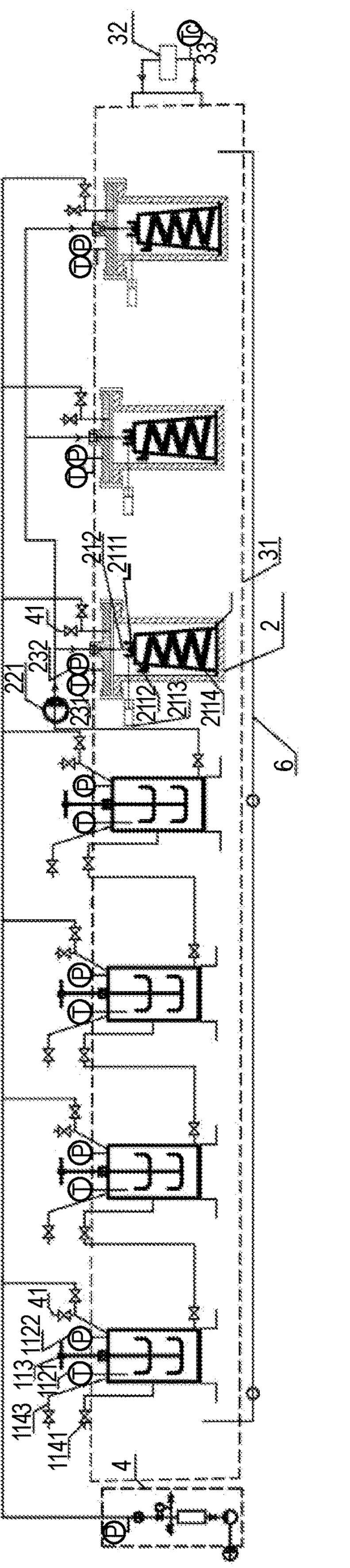
FIG. 5 is a schematic diagram of connection of an automatic microorganism isolation and purification process according to an example of the present invention.

In a specific implementation process, the survival activity of the microorganisms is improved by constructing the high-pressure and extreme temperature environmental conditions under which the microorganisms live in the marine environment in the microbial liquid enrichment culture chambers 11 and the isolation and culture chamber 21. Functional microorganisms with higher purity under stress of targeted environmental conditions are obtained through multistage enrichment and liquid dilution culture, and single microorganisms are obtained by culture and isolation in combination with the isolation and culture chamber 21. At the same time, an efficient isolation process with different culture medium combinations may be formed by selectively combining the microbial liquid enrichment culture chambers 11 and isolation and culture chamber 21, as shown in FIG. 5.

Example 2

More specifically, on the basis of Example 1, technology for enrichment culture and isolation of the marine microorganisms in the high-pressure environment involved in the device provided by this solution mainly includes two steps: enrichment and isolation. First, after enrichment culture by the enrichment and multistage purification unit 1, a bacteria group with higher purity is obtained, and enters the gravity-type isolation and culture unit 2 under a pressure-holding condition for solid culture and isolation, and a pure culture strain is obtained by screening at the same time through a combination process of different culture media and environmental conditions. A specific implementation principle is as follows.

Enrichment: the microbial liquid enrichment culture chambers 11 and attached pipe valve members thereof are first sterilized, then substrates to be cultured, such as deep sea sediments, macro-biological tissues symbiotic with the microorganisms, and an extracting solution, are fed in sequence, then a nutrient solution required for culture is fed from the liquid inlet valves 1141, and then gas (inert gas may be injected if gas is not required) required for culture is injected from the gas inlet valves 1142, such that the pressure values in the microbial liquid enrichment culture chambers 11 are increased to be consistent with the actual environmental conditions in the deep sea. In the culture process, the manual stirring rods 113 on the top are used for stirring to enhance a mass transfer effect and optimize the culture process. After the culture process in a first microbial liquid enrichment culture chamber 11 is completed, a nutrient solution required for culture is injected into a second microbial liquid enrichment culture chamber 11, and gas is injected into the second microbial liquid enrichment culture chamber 11 through the pressure control system 4 for pressurization. The amount of the culture solution injected into the second microbial liquid enrichment culture chamber 11 needs to ensure that a dilution ratio of the concentration of an enrichment liquid from the first microbial liquid enrichment culture chamber 11 to the second microbial liquid enrichment culture chamber 11 meets purification requirements, and then the microbial bacteria liquid in the first microbial liquid enrichment culture chamber 11 is transferred to the second microbial liquid enrichment culture chamber 11 through pressure-holding transfer. On this basis, the microorganisms in the last microbial liquid enrichment culture chamber 11 may reach a highly purified state. When the concentration of the deep-sea microbial bacteria liquid in the last microbial liquid enrichment culture chamber 11 reaches $10^6$ cfu/mL or more, it may be considered that a desirable purification state is achieved. The dilution ratio at each stage may be regulated for a particular cultured microbial group.

After it is identified that the bacteria liquid concentration in the enrichment process meets the requirements, the isolation and culture process is started.

Isolation: first, the isolation and culture chamber 21 and all internal components and associated pipe valve members thereof are sterilized to maintain a sterile state. The guide chute 2114 in the surface of the microorganism isolation branch 211 is then filled with a culture medium required for culture. The removable reservoir 2111 is then placed on the top of the microorganism isolation branch 211. The reciprocating puller 2113 is then installed. The quick-open kettle lid 213 of the culture chamber is then installed to ensure that the central liquid injection pipe 212 is unblocked. Then gas is injected into the isolation and culture chamber 21 through the pressure control system 4 for pressurization, such that the pressure conditions in the isolation and culture chamber 21 are consistent with the pressure conditions in the microbial liquid enrichment culture chambers 11. After ensuring normal operation of all system components, the microinjection pump 221 is turned on to inject a small amount of marine microorganism enrichment bacteria liquid into the removable reservoir 2111 on the microorganism isolation branch 211 from the last microbial liquid enrichment culture chamber 11 through the central liquid injection pipe 212, such that the marine microorganism enrichment bacteria liquid is uniformly dispersed on the pellet 2112. Then, the reciprocating puller 2113 is started to drag the removable reservoir 2111 at the stop box 2116 of the guide chute 2114 on the side face of the circular truncated cone. Since the diameter of the pellet 2112 is smaller than the diameter of the hole in the bottom of the removable reservoir 2111, the pellet 2112 may be released from the removable reservoir 2111 into the guide chute 2114, and may spiral from top to bottom in the guide chute 2114 and move to the bottom under the action of gravity. The enriched bacteria liquid on the pellet 2112 may be dispersed in the guide chute 2114 to meet the isolation and purification culture process. Along a trajectory of movement of the pellet 2112, a streaking trajectory of the bacteria liquid may be gradient dilution, and isolated colonies may grow along a guide trajectory. At this moment, the isolation process is completed.

Example 3

Preferably, as shown in FIG. 5, a plurality of isolation and culture chambers 21 are disposed in sequence, and the liquid injection unit 22 is connected to the central liquid injection pipes 212 of all the isolation and culture chambers 21. The temperature controlling system 3 and the pressure control system 4 are connected to all the isolation and culture chambers 21 respectively for constructing the high-pressure and low-temperature environment consistent with the marine environment in each of the isolation and culture chambers 21, so as to ensure that the enriched deep-sea microorganisms are isolated and cultured under the in-situ environmental conditions. Each of the isolation and culture chambers 21 is connected to an independent environmental parameter detection unit 23 for real-time monitoring of temperature and pressure changes in the isolation and culture chamber 21 and transmission of detected data to the central control system 5.

In a specific implementation process, a microorganism isolation process involved in this example is mainly a process in which the plurality of isolation and culture chambers 21 are placed in parallel, and inlets of all the isolation and culture chambers 21 are connected in parallel by piping and connected to the microinjection pump 221 and the last microbial liquid enrichment culture chamber 11.

In order to facilitate selection of an optimal culture method, culture media of different formulations may be placed in different culture chambers. All the isolation and culture chambers 21 and pipe valve members involved in the culture process are then integrally sterilized, and then whether microorganism isolation branches 211, pellets 2112, reciprocating pullers 2113, guide chutes 2114, central liquid injection pipes 212, and accessory systems thereof in all the culture chambers are properly installed is checked. Then, by monitoring the temperature and pressure, it is ensured that the temperature and pressure environmental conditions in all the isolation and culture chambers 21 are consistent with the temperature and pressure environmental conditions of the marine environment in which the microorganisms are located. The microinjection pumps 221, the regulating valves 46, the central liquid injection pipes 212, and the reciprocating pullers 2113 are started in sequence, and the pellets 2112 may carry the bacteria liquid to move in the guide chute 2114 of the microorganism isolation branch 211 in each of the isolation and culture chambers 21. By automatic separation and combination of a large number of culture chambers, an automatic sorting process in different culture medium environments may be achieved, thereby effectively ensuring isolation, culture and purification of the microorganisms in the high-pressure environment, and providing a key technology for efficient utilization of the marine microorganisms and a sorting process in the high-pressure environment. Data acquisition, integration and display of parameter conditions in the whole culture process may be carried out through the central control system.

This example relates to the device and process for enrichment culture and gravity-type isolation of the marine microorganisms in the high-pressure environment, proposes multistage enrichment culture and multi-culture medium automatic isolation and purification culture of the marine microorganisms under the high-pressure and extreme temperature environmental conditions, and solves the problem that as an existing indoor pure culture technology and method are out of the high-pressure and extreme temperature environmental conditions where the marine microorganism live, a large number of microorganisms cannot be purely cultured. This example does not require professional operators, can be used in research laboratories, research vessels and other culture scenarios, and has high adaptability. This solution does not require professional personnel to perform manual enrichment and streaking isolation, and can perform large-scale enrichment and sorting, thereby reducing labor costs, realizing automatic isolation and culture of the marine microorganisms under in-situ pressure and temperature environmental conditions, and providing an important technical means for pure culture of the marine microorganisms under in-situ conditions.

Compared with the existing pure culture technology, this example proposes high-pressure pure culture technology for enrichment and isolation and culture of the marine microorganisms under the marine in-situ high-pressure and extreme temperature environmental conditions, which solves the problem that most microorganisms cannot be isolated and purely cultured because the existing atmospheric pressure isolation and culture technology is detached from the temperature and pressure environmental conditions in which the marine microorganisms live in situ. Compared with the existing isolation and culture technology, this solution can effectively reduce the input of professional personnel, and can perform large-scale enrichment and isolation and culture, thereby improving the screening efficiency of difficult-to-culture microorganisms, and improving the screening and cultivation efficiency of engineering bacteria with special functions.

Example 4

In order to further illustrate the technical implementation process and technical effects of this solution, this example provides a device for enrichment culture and isolation of deep-sea methanotrophs in a high-pressure environment. The device for enrichment culture and isolation of the deep-sea methanotrophs in the high-pressure environment involved in this example mainly includes two steps: enrichment and isolation. First, the deep-sea methanotrophs are enriched through a microbial liquid enrichment culture chamber 11, and passes through the next microbial liquid enrichment culture chamber 11 under a pressure-holding condition, a deep-sea methanotroph group with higher purity is obtained and then enters isolation and culture chambers 21 for isolation and culture, and finally single strains are obtained.

As for a method for enrichment culture of the deep-sea methanotrophs in the high-pressure environment involved in this example, first, the microbial liquid enrichment culture chamber 11 and attached pipe valve members thereof are sterilized; after the sterilization process is completed, each device is connected in sequence; sediments in a deep-sea methane seepage area are loaded into the microbial liquid enrichment culture chamber 11; a nutrient solution required for culture is fed; gas inlet valves 1142 are opened to inject methane gas required for culture through a pressure control system 4, such that a pressure value in the microbial liquid enrichment culture chamber 11 is increased to 14 Mpa, and is monitored by a pressure sensor 1122; meanwhile, the whole device is placed in a water bath jacket 31 of 4° C., and is displayed by a water bath temperature detection device 33 and exchanged with a refrigerating/heating device 32; and a water bath system is filled with a refrigerant such as ethylene glycol to maintain a low-temperature state in the microbial liquid enrichment culture chamber 11, and the temperature in the microbial liquid enrichment culture chamber 11 is monitored through a temperature sensor 1121. In order to ensure that the culture environment is an anaerobic environment, methane may be continuously fed for 5-10 min by opening a bleed valve 41. In the culture process, manual stirring rods 113 on a top of the microbial liquid enrichment culture chamber 11 are used for stirring to enhance a mass transfer effect and optimize the culture process. After the enrichment culture process in the microbial liquid enrichment culture chamber 11 is completed, the nutrient solution required for culture is injected into the next microbial liquid enrichment culture chamber 11, and the microbial liquid enrichment culture chamber is pressurized in the same method as in the former microbial liquid enrichment culture chamber 11. The amount of the culture solution injected into the microbial liquid enrichment culture chamber 11 needs to ensure that a dilution ratio of the concentration of the enrichment liquid from a first microbial liquid enrichment culture chamber 11 to the next microbial liquid enrichment culture chamber 11 is 1:10, then the pressure of a second microbial liquid enrichment culture chamber 11 is increased to be 0.2-0.5 MPa smaller than the pressure of the first microbial liquid enrichment culture chamber 11, then a liquid outlet valve 1144 of the first microbial liquid enrichment culture chamber 11 and a liquid inlet valve 1141 of the second microbial liquid enrichment culture chamber 11 are opened, and the microbial enrichment liquid may automatically enter the latter microbial liquid enrichment culture chamber 11 from the former microbial liquid enrichment culture chamber 11 for purification culture under the condition of a small pressure difference. On this basis, the microbial enrichment liquid is transferred into third and fourth microbial liquid enrichment culture chambers 11, and when the number of cells in the fourth microbial liquid enrichment culture chamber 11 reaches $10^6$ cells per mL or more and the abundance of the deep-sea methanotrophs is 50% or more, it may be considered that a desirable purification state is achieved. The dilution ratio at each stage may be regulated for a particular cultured microbial group. During an experiment, sampling and monitoring of the bacteria liquid required are carried out by opening a sampling valve 1143.

After it is identified that the bacteria liquid concentration in the fourth microbial liquid enrichment culture chamber 11 meets the requirement, the isolation and culture process is started. The isolation and culture process mainly includes: first, the isolation and culture chamber 21 and all internal components and associated pipe valve members thereof are sterilized. Guide chutes 2114 in microorganism isolation branches 211 are then filled with culture media required for culture. Removable reservoir 2111 are disposed on tops of the microorganism isolation branches 211. Pellets 2112 are placed in slots inside the removable reservoirs 2111 to be prevented from sliding. Reciprocating pullers 2113 are then installed. Upper lids of the isolation and culture chambers 21 and central liquid injection pipes 212 are then installed. Then gas is injected into the isolation and culture chambers 21 through the pressure control system 4 for pressurization, such that the pressure conditions in the isolation and culture chambers 21 are consistent with the pressure conditions in the microbial liquid enrichment culture chambers 11. After ensuring normal operation of all system components, a microinjection pump 221 is started to inject 10 microlitres of microorganism enrichment liquid into the removable reservoirs 2111 on the microorganism isolation branches 211 from the last microbial liquid enrichment culture chamber through the central liquid injection pipes 212, such that the microorganism enrichment liquid is uniformly dispersed on the pellets 2112. Then, the reciprocating pullers 2113 are started to drag the removable reservoirs 2111 at the guide chutes 2114 at the side faces of the microorganism isolation branches 211. Since a diameter of the pellets 2112 is smaller than a diameter of holes in bottoms of the removable reservoirs 2111, the pellets 2112 may be released from the removable reservoirs 2111 into the guide chutes 2114, and may spiral from top to bottom in the guide chutes 2114 and move to the bottom under the action of gravity. A streaking trajectory of the enrichment bacteria liquid on the pellets 2112 may be gradient dilution, and microorganisms may grow into isolated colonies along a guide trajectory.

In an automatic isolation and purification process for the deep-sea methanotrophs involved in this example, the plurality of isolation and culture chambers 21 are placed in parallel, and inlets of all the isolation and culture chambers 21 are connected in parallel by piping and connected to the microinjection pump 221 and an enrichment and multistage purification unit 1. In order to facilitate selection of an optimal culture method, culture media of different formulations may be placed in different culture chambers. All the culture chambers and pipe valve members involved in the culture process are then integrally sterilized, and whether the microorganism isolation branches 211, the pellets 2112, the reciprocating pullers 2113, the guide chutes 2114, the central liquid injection pipes 212, and accessory systems thereof in all the culture chambers are properly installed is checked. By monitoring the temperature and pressure, it is ensured that the temperature and pressure environmental conditions in all the culture chambers are 4° C. and 14 MPa. The microinjection pumps 221, regulating valves 46, the central liquid injection pipes 212, and the reciprocating pullers 2113 are started in sequence, and the pellets 2112 may carry the bacteria liquid to move in the guide chute 2114 of the microorganism isolation branch 211 in each of the isolation and culture chambers 21. By automatic separation and combination of a large number of culture chambers, an automatic isolation process in different culture medium environments may be achieved, thereby effectively ensuring isolation, culture and purification of the microorganisms in the high-pressure environment, and providing a key technology for efficient utilization of the marine microorganisms and a sorting process in the high-pressure environment. Data acquisition, integration and display of parameter conditions in the whole culture process may be carried out through a central control system 5. A mobile platform 6 is additionally installed at a bottom of the device for enrichment culture and isolation as a whole for improving general adaptability to a culture scenario.

In a specific implementation process, the enrichment and multistage purification unit 1 may achieve enrichment culture of the microorganisms under marine in-situ temperature and pressure environmental conditions, and the gravity-type isolation and culture unit 2 may achieve isolation and culture of the marine microorganisms. By reconstructing the in-situ environment for enrichment culture and isolation of the marine microorganisms, the problem about isolation and pure culture of the marine microorganisms in the high-pressure environment is solved, culturability of the marine microorganisms is effectively improved, and an important basic means is provided for development and utilization of deep-sea microorganism resources.

It is apparent that the above embodiments of the present invention are merely examples of the present invention for purposes of clarity and are not intended to limit the implementations of the present invention. Changes or modifications in other different forms can also be made by those of ordinary skill in the art on the basis of the above description. All implementations need not to be, and cannot be, exhaustive. Any modifications, equivalent replacements, improvements, etc. made within the spirit and principle of the present invention shall fall within the protection scope of the claims of the present invention.

What is claimed is:

1. A device for enrichment culture and gravity isolation of marine microorganisms in a high-pressure environment, wherein the high-pressure environment is a pressure environment at a water depth greater than 200 meters in a deep sea, the device comprises an enrichment and multistage purification unit, a gravity isolation and culture unit, a temperature controlling system, a pressure control system, and a central control system, wherein the central control system includes a processor to control the temperature controlling system and the pressure control system, wherein control ends and signal detection ends of the enrichment and multistage purification unit and the gravity isolation and culture unit are electrically connected to the central control system; control ends of the temperature controlling system and the pressure control system are electrically connected to the central controller control system; wherein, the enrichment and multistage purification unit is used for realizing a process of enrichment and multistage purification of the marine microorganisms, obtaining a marine microorganism enrichment bacteria liquid, and injecting the marine microorganism enrichment bacteria liquid into the gravity isolation and culture unit;

the gravity isolation and culture unit is used for carrying out automatic streaking by means of gravity in the high-pressure environment to achieve solid isolation and culture of the marine microorganisms, such that culturability of the marine microorganisms is effectively improved;

the temperature controlling system and the pressure control system are connected to the enrichment and multistage purification unit and the gravity isolation and culture unit respectively for constructing a high-pressure and low-temperature environment consistent with a marine environment in the enrichment and multistage purification unit and the gravity isolation and culture unit, so as to ensure that enriched deep-sea microorganisms are enriched, purified, separated and cultured under in-situ environmental conditions, wherein the high-pressure and low-temperature environment is environment at a water depth greater than 200 meters and below 4° C. in a deep sea;

wherein, the pressure control system comprises a bleed valve, an air compressor, a booster pump, a gas storage tank, a pressure regulating valve, a regulating valve, and a vent pipeline; wherein, the bleed valve is connected to the enrichment and multistage purification unit and the gravity isolation and culture unit through the vent pipeline, and a control end of the bleed valve is electrically connected to the central control system for discharging gas from the enrichment and multistage purification unit and the gravity isolation and culture unit, and for depressurizing interior of the enrichment and multistage purification unit and the gravity isolation and culture unit;

the air compressor, the booster pump, the gas storage tank, the pressure regulating valve and the regulating valve are connected in sequence through the vent pipeline, and finally connected to the enrichment and multistage purification unit and the gravity isolation and culture unit through the vent pipeline for filling the enrichment and multistage purification unit and the gravity isolation and culture unit with gas for pressurization; the pressure regulating valve is used for regulating internal pressure of the enrichment and multistage purification unit and the gravity isolation and culture unit; the regulating valve is used for regulating a speed of gas injection;

a control end of the air compressor, a control end of the booster pump, a control end of the pressure regulating valve, and a control end of the regulating valve are electrically connected to the central control system;

the temperature controlling system comprises a water bath jacket and a heat exchanger; the water bath jacket is wrapped on outer walls of the enrichment and multistage purification unit and the gravity isolation and culture unit, and is connected to the water bath heat exchanger; and a control end of the heat exchanger is electrically connected to the central control system; the temperature controlling system further comprises a thermocouple, and an output end of the thermocouple is electrically connected to the central control system for detecting the water bath temperature in the water bath jacket in real time, so as to facilitate real-time temperature regulation;

the enrichment and multistage purification unit comprises a plurality of microbial liquid enrichment culture chambers connected in series; the microbial liquid enrichment culture chambers are provided with removable sealing lids and connection and sampling valve sets, and sensor sets are disposed inside the microbial liquid enrichment culture chambers; each of the microbial liquid enrichment culture chambers is disposed in the temperature controlling system; wherein, the removable sealing lids are used for facilitating sterilization operations and placement of culture substrates inside the microbial liquid enrichment culture chambers;

the connection and sampling valve sets are used for connection and sampling of the microbial liquid enrichment culture chambers, and are connected to the pressure control system for feeding liquid or gas into the microbial liquid enrichment culture chambers to increase pressure inside the microbial liquid enrichment culture chambers, such that pressure values in the microbial liquid enrichment culture chambers are consistent with pressure values in the pressure environment at the water depth greater than 200 meters in the deep sea;

the sensor sets are used for real-time monitoring of temperature and pressure changes in the microbial liquid enrichment culture chambers, and transmitting signals to the central control system; and a last microbial liquid enrichment culture chamber of the enrichment and multistage purification unit is connected to the gravity isolation and culture unit through the connection and sampling valve sets;

the gravity isolation and culture unit comprises at least one isolation and culture chamber, a liquid injection unit, and an environmental parameter detection unit; wherein, the liquid injection unit comprises a microinjection pump and a liquid injection pipeline, and the environmental parameter detection unit comprises a second temperature sensor and a second pressure sensor, the gravity isolation and culture unit is connected to the last microbial liquid enrichment culture chamber of the enrichment and multistage purification unit through the liquid injection unit;

a microorganism isolation branch is disposed in the at least one isolation and culture chamber for carrying out an isolation operation on microorganisms to provide a maximum area for microorganism culture;

a central liquid injection pipe is disposed on a top of the at least one isolation and culture chamber, and the at least one isolation and culture chamber is connected to the liquid injection unit through the central liquid injection pipe; a marine microorganism enrichment bacteria liquid is injected by the liquid injection unit into the microorganism isolation branch of the at least one isolation and culture chamber;

the at least one isolation and culture chamber is disposed in the temperature controlling system and connected to the pressure control system for constructing the high-pressure and low-temperature environment consistent with the marine environment in the at least one isolation and culture chamber, so as to ensure that the enriched deep-sea microorganisms are isolated and cultured in the in-situ environmental condition;

the environmental parameter detection unit is used for real-time detection of temperature and pressure changes in the at least one isolation and culture chamber and transmission of detected data to the central control system; and the microorganism isolation branch and the liquid injection unit are electrically connected to the central control system;

the microorganism isolation branch comprises a removable reservoir, a pellet, a reciprocating puller, a guide chute, and a cavity; wherein, the removable reservoir is disposed in a center of a top of the cavity, and located under the central liquid injection pipe for storing the marine microorganism enrichment bacteria liquid injected by the liquid injection unit; the pellet is placed in the removable reservoir and submerged by the injected marine microorganism enrichment bacteria liquid; a through hole is provided in a bottom of the removable reservoir for fixing a position of the pellet and ensuring that the pellet is able to pass through the through hole; a movable end of the reciprocating puller is fixedly connected to the removable reservoir; a stop box is disposed on an outer surface of the top of the cavity; a control end of the reciprocating puller is electrically connected to the central control system the guide chute is fixedly disposed inside the cavity; the guide chute is filled with a culture medium, and an inlet of the guide chute communicates with the stop box;

after the pellet is submerged in the marine microorganism enrichment bacteria liquid, the removable reservoir moves toward an edge of the cavity under action of the reciprocating puller; when the through hole of the removable reservoir leaves the cavity, the pellet passes through the through hole and falls into the stop box of the cavity due to gravity, and enters the guide chute inside the cavity; and while the pellet carries the marine microorganism enrichment bacteria liquid to slide along the guide chute from top to bottom, the marine microorganism enrichment bacteria liquid is dispersed through concentration gradient dilution to provide the maximum area for microorganism isolation and culture.

2. The device for enrichment culture and gravity isolation of marine microorganisms in a high-pressure environment according to claim 1, wherein the microbial liquid enrichment culture chambers are further provided with stirring rods, and the stirring rods are used for enhancing a reaction process of a substrate in a culture process of the microbial liquid enrichment culture chambers.

3. The device for enrichment culture and gravity isolation of marine microorganisms in a high-pressure environment according to claim 1, wherein the sensor sets comprise second temperature sensors and second pressure sensors; the second temperature sensors are used for real-time monitoring of temperature changes in the microbial liquid enrichment culture chambers; the second pressure sensors are used for real-time monitoring of pressure changes in the microbial liquid enrichment culture chambers; and signal output ends of the second temperature sensors and signal output ends of the second pressure sensors are electrically connected to the central control system.

4. The device for enrichment culture and gravity isolation of marine microorganisms in a high-pressure environment according to claim 1, wherein the connection and sampling valve sets comprise liquid inlet valves, gas inlet valves, sampling valves, and liquid outlet valves; wherein, the microbial liquid enrichment culture chambers are connected in series through the liquid outlet valves and the liquid inlet valves, and a liquid outlet valve of a former microbial liquid enrichment culture chamber is connected to a liquid inlet valve of a latter microbial liquid enrichment culture chamber; a liquid outlet valve of the last microbial liquid enrichment culture chamber is connected to the gravity isolation and culture unit;

the gas inlet valves are connected to the pressure control system for feeding gas into the microbial liquid enrichment culture chambers to increase the pressure in the microbial liquid enrichment culture chambers, such that the pressure values in the microbial liquid enrichment culture chambers are consistent with the pressure values in the pressure environment at the water depth greater than 200 meters in the deep sea; and the sampling valves are used for real-time sampling and analysis of the microorganisms in the microbial liquid enrichment culture chambers.

5. The device for enrichment culture and gravity isolation of marine microorganisms in a high-pressure environment according to claim 1, wherein a slot is provided in the center of the top of the cavity, that is, a position where an initial position of the removable reservoir coincides with the through hole, for fixing the position of the pellet.

6. The device for enrichment culture and gravity isolation of marine microorganisms in a high-pressure environment according to claim 1, wherein, a liquid inlet end of the microinjection pump is connected to the last microbial liquid enrichment culture chamber of the enrichment and multistage purification unit, and a liquid outlet end of the microinjection pump is connected to the liquid injection pipeline; a liquid outlet of the liquid injection pipeline is connected to the central liquid injection pipe; and a control end of the microinjection pump is electrically connected to the central control system.

7. The device for enrichment culture and gravity isolation of marine microorganisms in a high-pressure environment according to claim 1, wherein, probes of the second temperature sensor and the second pressure sensor are disposed inside the at least one isolation and culture chamber, and signal output ends of the second temperature sensor and the second pressure sensor are electrically connected to the central control system.

8. The device for enrichment culture and gravity isolation of marine microorganisms in a high-pressure environment according to claim 7, wherein a quick-open kettle lid is disposed on the top of the at least one isolation and culture chamber; the central liquid injection pipe is disposed on the quick-open kettle lid; the quick-open kettle lid is further provided with a gas injection channel and a sensor containing channel; the pressure control system is connected to the at least one isolation and culture chamber through the gas injection channel; and the second temperature sensor and the second pressure sensor are disposed in the sensor containing channel.

9. The device for enrichment culture and gravity isolation of marine microorganisms in a high-pressure environment according to claim 1, wherein the at least one isolation and culture chamber includes a plurality of isolation and culture chambers disposed in sequence, the central liquid injection pipe comprises a plurality of sub-central liquid injection pipes and the liquid injection unit is connected to the plurality of sub-central liquid injection pipes of all the plurality of isolation and culture chambers; the temperature controlling system and the pressure control system are connected to all the plurality of isolation and culture chambers respectively for constructing the high-pressure and low-temperature environment consistent with the marine environment in each of the plurality of isolation and culture chambers, so as to ensure that the enriched deep-sea microorganisms are isolated and cultured under the in-situ environmental condition; and each of the plurality of isolation and culture chambers is connected to an independent environmental parameter detector for real-time detection of temperature and pressure changes in each of the plurality of isolation and culture chambers and transmission of detected data to the central control system.

10. The device for enrichment culture and gravity isolation of marine microorganisms in a high-pressure environment according to claim 9, wherein the device further comprises a mobile platform, wherein the enrichment and multistage purification unit, the gravity isolation and culture unit, the temperature controlling system, the pressure control system, and the central control system are placed on the mobile platform for improving general applicability to a culture scenario.

11. The device for enrichment culture and gravity isolation of marine microorganisms in a high-pressure environment according to claim 5, wherein the at least one isolation and culture chamber includes a plurality of isolation and culture chambers disposed in sequence, the central liquid injection pipe comprises a plurality of sub-central liquid injection pipes and the liquid injection unit is connected to the plurality of sub-central liquid injection pipes of all the plurality of isolation and culture chambers; the temperature controlling system and the pressure control system are connected to all the plurality of isolation and culture chambers respectively for constructing the high-pressure and low-temperature environment consistent with the marine environment in each of the plurality of isolation and culture chambers, so as to ensure that the enriched deep-sea microorganisms are isolated and cultured under the in-situ environmental condition; and each of the plurality of isolation and culture chambers is connected to an independent environmental parameter detector for real-time detection of temperature and pressure changes in each of the plurality of isolation and culture chambers and transmission of detected data to the central control system.

12. The device for enrichment culture and gravity isolation of marine microorganisms in a high-pressure environment according to claim 9, wherein the at least one isolation and culture chamber includes a plurality of isolation and culture chambers disposed in sequence, the central liquid injection pipe comprises a plurality of sub-central liquid injection pipes and the liquid injection unit is connected to the plurality of sub-central liquid injection pipes of all the plurality of isolation and culture chambers; the temperature controlling system and the pressure control system are connected to all the plurality of isolation and culture chambers respectively for constructing the high-pressure and low-temperature environment consistent with the marine environment in each of the plurality of isolation and culture chambers, so as to ensure that the enriched deep-sea microorganisms are isolated and cultured under the in-situ environmental condition; and each of the plurality of isolation and culture chambers is connected to an independent environmental parameter detector for real-time detection of temperature and pressure changes in each of the plurality of isolation and culture chambers and transmission of detected data to the central control system.

13. The device for enrichment culture and gravity isolation of marine microorganisms in a high-pressure environment according to claim 10, wherein the at least one isolation and culture chamber includes a plurality of isolation and culture chambers disposed in sequence, the central liquid injection pipe comprises a plurality of sub-central liquid injection pipes and the liquid injection unit is connected to the plurality of sub-central liquid injection pipes of all the plurality of isolation and culture chambers; the temperature controlling system and the pressure control system are connected to all the plurality of isolation and culture chambers respectively for constructing the high-pressure and low-temperature environment consistent with the marine environment in each of the plurality of isolation and culture chambers, so as to ensure that the enriched deep-sea microorganisms are isolated and cultured under the in-situ environmental condition; and each of the plurality of isolation and culture chambers is connected to an independent environmental parameter detector for real-time detection of temperature and pressure changes in each of the plurality of isolation and culture chambers and transmission of detected data to the central control system.

14. The device for enrichment culture and gravity isolation of marine microorganisms in a high-pressure environment according to claim 11, wherein the at least one isolation and culture chamber includes a plurality of isolation and culture chambers disposed in sequence, the central liquid injection pipe comprises a plurality of sub-central liquid injection pipes and the liquid injection unit is connected to the plurality of sub-central liquid injection pipes of all the plurality of isolation and culture chambers; the temperature controlling system and the pressure control system are connected to all the plurality of isolation and culture chambers respectively for constructing the high-pressure and low-temperature environment consistent with the marine environment in each of the plurality of isolation and culture chambers, so as to ensure that the enriched deep-sea microorganisms are isolated and cultured under the in-situ environmental condition; and each of the plurality of isolation and culture chambers is connected to an independent environmental parameter detector for real-time detection of temperature and pressure changes in each of the plurality of isolation and culture chambers and transmission of detected data to the central control system.

* * * * *